(12) United States Patent
Tang et al.

(10) Patent No.: US 11,890,362 B2
(45) Date of Patent: *Feb. 6, 2024

(54) ORAL CARE COMPOSITION

(71) Applicant: Colgate-Palmolive Company, New York, NY (US)

(72) Inventors: Saide Tang, Princeton, NJ (US); Lin Fei, Kendall Park, NJ (US); Suman Chopra, Monroe, NJ (US); Hallena Strotman, Somerset, NJ (US); Pooja Kulkarni, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/851,291

(22) Filed: Apr. 17, 2020

(65) Prior Publication Data

US 2020/0352834 A1     Nov. 12, 2020

Related U.S. Application Data

(60) Provisional application No. 62/843,710, filed on May 6, 2019.

(51) Int. Cl.
*A61K 8/25* (2006.01)
*A61K 8/04* (2006.01)
*A61Q 11/00* (2006.01)

(52) U.S. Cl.
CPC ............... *A61K 8/25* (2013.01); *A61K 8/042* (2013.01); *A61Q 11/00* (2013.01); *A61K 2800/651* (2013.01)

(58) Field of Classification Search
CPC .... A61K 8/25; A61K 8/042; A61K 2800/651; A61K 2800/621; A61K 2800/63; A61K 8/0241; A61K 8/27; A61Q 11/00
See application file for complete search history.

(56) References Cited

U.S. PATENT DOCUMENTS

| | | | |
|---|---|---|---|
| 4,075,317 | A | 2/1978 | Mitchell et al. |
| 5,603,920 | A | 2/1997 | Rice |
| 6,149,894 | A | 11/2000 | Yamane et al. |
| 7,166,272 | B2 | 1/2007 | Fujisawa |
| 9,974,723 | B2 | 5/2018 | D'Ambrogio et al. |
| 10,004,676 | B2 | 6/2018 | Ibrahim |
| 10,532,012 | B2 | 1/2020 | Tang |
| 10,596,084 | B2 | 3/2020 | Maloney |
| 2003/0175345 | A1 | 9/2003 | Federici |
| 2016/0331653 | A1 | 11/2016 | Maloney |
| 2016/0338919 | A1* | 11/2016 | Pan .................... C03C 17/23 |
| 2018/0168965 | A1 | 6/2018 | Kocinska et al. |
| 2018/0280264 | A1 | 10/2018 | Rege |
| 2019/0008746 | A1 | 1/2019 | Leonhardt |

FOREIGN PATENT DOCUMENTS

| | | |
|---|---|---|
| CA | 2447841 | 1/2003 |
| CN | 105813620 | 7/2016 |
| CN | 105829574 | 8/2016 |
| CN | 107624064 | 1/2018 |
| WO | 2007/122146 | 11/2007 |
| WO | 2015/094152 | 6/2015 |
| WO | 2015/095709 | 6/2015 |
| WO | 2016/180620 | 11/2016 |
| WO | 2016/180621 | 11/2016 |
| WO | 2017/062021 | 4/2017 |
| WO | 2019/035839 | 2/2019 |
| WO | 2020/226876 | 11/2020 |

OTHER PUBLICATIONS

International Search Report and the Written Opinion of the International Searching Authority issued in International Application PCT/US2020/028638 dated Jun. 24, 2020.

\* cited by examiner

*Primary Examiner* — Snigdha Maewall

(57) ABSTRACT

Described herein are oral care compositions comprising metal silicates (e.g. sodium silicate); along with methods of making and using same.

17 Claims, No Drawings

ORAL CARE COMPOSITION

CROSS-REFERENCE TO RELATED APPLICATION

This application claims the benefit of priority from U.S. Provisional Application No. 62/843,710, filed May 6, 2019, the contents of which are hereby incorporated herein by reference in their entirety.

BACKGROUND

Certain individuals are dissatisfied with the color of their teeth. Thus, there is a significant market need for whiter teeth; and one method to achieve whiter teeth is the use of tooth whitening products. There are a range of tooth whitening products including toothpastes, gels, trays, strips, and professional treatments. Depending on the perceived needs of the consumer, different treatment types are favored. A growing number of consumers are expressing a desire for whitening regimens that are gentle on tooth enamel; and are shying away from more extreme and expensive professional treatments. Instead, they seek a safe and easy, inexpensive and effective option, for example, in a toothpaste.

The color of human teeth comes from the combined color of the enamel and dentin. Enamel is a semi-transparent material that covers human teeth and thins over the course of time. The natural color of teeth becomes more yellow over time due to this thinning along with the accumulation of stains. These stains may come from multiple sources, e.g. medication, diet, and lifestyle choices. There are two types of tooth stains—extrinsic and intrinsic; and different modes of action are required to target each type of stain. Extrinsic stains are usually removed through the mechanical action of an abrasive system in a toothpaste in combination with the brushing action of the toothbrush; whereas intrinsic stains are attacked with bleaching agents such as hydrogen peroxide that can penetrate the surface of the enamel.

Certain markets do not allow the use of hydrogen peroxide and other oxidizing agents in their dentifrices; yet consumers in these regions are still in need of products to meet their whitening needs. One way to deliver additional stain removal benefits without the use of oxidizing agents is to utilize novel abrasive systems and additives that boost the efficacy of those abrasive systems.

Embodiments of the present invention are directed to these, and other, ends.

BRIEF SUMMARY

In some embodiments, the present invention provides an oral care composition comprising: a first metal silicate; and an orally acceptable carrier; wherein the first metal silicate comprises a silicate of a monovalent or divalent metal ion. In other embodiments, the present invention further comprises: a core shell silica particle comprising; a second metal silicate; and a silica particle comprising a core having a surface; wherein the surface of the silica core is etched with the second metal silicate; and wherein the second metal silicate comprises a metal ion.

Further embodiments provide oral care compositions comprising: an orally acceptable carrier; a first metal silicate comprising a silicate of a monovalent metal ion; and a gel matrix; wherein the oral care composition has a pH of from about 8 to about 10.

Other embodiments provide methods of: a) reducing extrinsic stains on a mammalian tooth; b) whitening a mammalian tooth; c) reducing or preventing tartar; and/or d) removing extrinsic stains from a mammalian tooth; the method comprising: administering a composition according to any foregoing claim to an oral surface of a mammal in need thereof.

Still further embodiments provide for the use of any one of the compositions described herein in the manufacture of a medicament for: a) reducing extrinsic stains on a mammalian tooth; b) whitening a mammalian tooth; c) reducing or preventing tartar; and/or d) removing extrinsic stains from a mammalian tooth.

Further areas of applicability of the present invention will become apparent from the detailed description provided hereinafter. It should be understood that the detailed description and specific examples are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range, and for describing sub-ranges within the range. Any value within the range can be selected as the upper terminus of the sub-range. Any value within the range can be selected as the lower terminus of the sub-range.

In addition, all references, books, patents, and patent application publications cited herein are hereby incorporated by reference in their entireties. In the event of a conflict in a definition in the present disclosure and that of a cited reference, book, patent, or patent application publication, the present disclosure controls.

Unless otherwise specified, reference to ambient or room temperature refers to a temperature range of 20-25° C.

Unless otherwise specified, all percentages and amounts expressed herein and elsewhere in the specification should be understood to refer to percentages by weight based on the total weight of the composition.

The phrase "and/or" as used herein, with option A and/or option B for example, encompasses the individual embodiments of (i) option A; (ii) option B; and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

In some embodiments, the present invention provides oral care compositions comprising: a first metal silicate; and an orally acceptable carrier; wherein the first metal silicate comprises a silicate of a monovalent or divalent metal ion. In some embodiments, the first metal silicate comprises a silicate of a monovalent metal ion. In other embodiments, the first metal silicate consists essentially of a monovalent metal ion. In further embodiments, the first metal silicate consists of a monovalent metal ion and a silicone or a derivative thereof. In some embodiments, the first metal silicate comprises a silicate of a monovalent metal ion selected from Na+ and K+. In some embodiments, the monovalent metal ion comprises Na+. In some embodiments, the monovalent metal ion comprises K+.

In some embodiments, the oral care composition further comprises: a core shell silica particle comprising; a second metal silicate; and a silica particle comprising a core having a surface; wherein the surface of the silica core is etched with the second metal silicate; and wherein the second metal silicate comprises a metal ion. As used herein, the term "etched" means that a surface of the silica core is dissolved, and the metal silicate is formed adjacent to the silica core. The process for making the core shell silica particles comprises etching the original silica in order to form the metal silicate. The layer(s) of second metal silicate do not form on top of the original surface of the silica core. Rather, the reaction of the silica particle with base causes a reduction in the diameter of the original silica particle and the second metal silicate layer forms on top of the surface of etched silica particle having a reduced diameter.

In some embodiments, the second metal silicate comprises a silicate of a monovalent, or multivalent metal ion. In other embodiments, the multivalent metal ion is selected from: $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$; and a combination of two or more thereof. In further embodiments, the multivalent metal ion is a divalent metal ion selected from $Ca^{2+}$, $Mg^{2+}$, $Zn^{2+}$, $Sn^{2+}$, $Sr^{2+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, and $Ru^{2+}$. In certain embodiments, the multivalent metal ion is selected from $Zn^{2+}$ and $Sn^{2+}$.

In some embodiments, the second metal silicate further comprises a monovalent metal ion. In some embodiments, the monovalent metal ion of the second metal silicate is selected from Na+ and K+. Further embodiments provide compositions wherein the second metal silicate comprises a monovalent metal ion is K+.

In some embodiments, the silica is selected from: precipitated silica; fumed silica; heat treated precipitated silica; and fused silica.

In some embodiments, the silica is fumed silica. Pyrogenic silica (sometimes called fumed silica or silica fume) is a very fine particulate or colloidal form of silicon dioxide. It is prepared by burning $SiCl_4$ in an oxygen rich hydrocarbon flame to produce a "smoke" of $SiO_2$. The silica particles fuse with one another to form branched, three-dimensional chain-like aggregates:

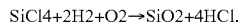
$SiCl_4 + 2H_2 + O_2 \rightarrow SiO_2 + 4HCl$.

In some embodiments, the silica is precipitated silica. Amorphous silica, silica gel, is produced by the acidification of solutions of sodium silicate. An initially formed gelatinous precipitate is then washed and then dehydrated to produce colorless microporous silica. Idealized equation involving a trisilicate and sulfuric acid is shown:

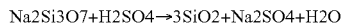
$Na_2Si_3O_7 + H_2SO_4 \rightarrow 3SiO_2 + Na_2SO_4 + H_2O$

In the majority of silicas, the Si atom shows tetrahedral coordination, with 4 oxygen atoms surrounding a central Si atom. The most common example is seen in the quartz crystalline form of silica $SiO_2$. In each of the most thermodynamically stable crystalline forms of silica, on average, all 4 of the vertices (or oxygen atoms) of the $SiO_4$ tetrahedra are shared with others, yielding the net chemical formula: $SiO_2$. $SiO_2$ has a number of distinct crystalline forms (polymorphs) in addition to amorphous forms. With the exception of stishovite and fibrous silica, all of the crystalline forms involve tetrahedral $SiO_4$ units linked together by shared vertices in different arrangements.

Precipitated silica includes, but is not limited to Zeodent® 114 and Zeodent® 165 (precipitated silica particles produced by J.M. Huber—synthetic amorphous silica), Sylodent® 783 produced by W.R. Grace, Sorbosil® AC-43 produced by Ineos (PQ Corp.)

The silica may be a fumed silica, such as Aerosil 200, produced by Evonik.

In another embodiment, the silica is a fused silica, which includes but is not limited to CAB-O-SIL® HP-60, produced by Cabot Corporation, TECO-SIL® 10 and TECO-SIL® 44css, produced by C-E Minerals, and Spheron P1500 made by the Japanese Glass Co.

The oral care composition according to any foregoing claim, wherein the core shell particle comprises a plurality of metal silicate layers. In some embodiments the core shell silica particle comprises from about 2 to about 100, about 2 to about 40, about 2 to about 12, or about 12 to about 40, metal silicate layers. In further embodiments, the core shell silica particle may comprise 2, 4, 16, 32, 36 or 64 monolayers.

In some embodiments, the second metal silicate comprises $ZnSiO_3 \cdot xH_2O$, wherein x is from 0 to 10.

In one embodiment the surface of the silica core is the outer surface of the silica core. In addition or as an alternative the surface of the silica core may be an internal surface of the silica core.

The silicate of the second metal ion may comprise at least 30 weight %, 40 weight % 50 weight % 60 weight %, 70 weight %, 80 weight % or 90 weight % of the total metal silicate of the CSS particles. Preferably, the silicate of the second metal ion comprises at least 90 weight % of the total metal silicate of the CSS particles.

In some embodiments, the outer 10 nm depth of the core shell silica particle may comprise from 0.1 to 10 weight % metal silicate. In some embodiments the outer 10 nm depth of the core shell silica particle has the general formula: wherein O* is oxygen in the silicate form; N is a monovalent metal ion; M is a divalent metal ion; U is a trivalent metal ion; V is a tetravalent metal ion; p, o, n, m, u, v, h and q are the atomic percentages of each component; and the total charge of each core shell silica particle is zero.

The atomic percentage for each component except H+ is typically determined by electron spectroscopy for chemical analysis (ESCA). In one example, using ESCA data, the following elements were detected:

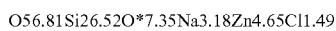
$O56.81Si26.52O*7.35Na3.18Zn4.65Cl1.49$

By setting the total electric charge to zero by adding H+ and water, we conclude that in one embodiment the outer 10 nm depth of each particle may have the following composition:

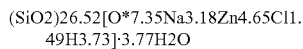
$(SiO_2)26.52[O*7.35Na3.18Zn4.65Cl1.49H3.73] \cdot 3.77H_2O$

The d(0.5) value of the particles is typically from 5 nm to 50 μm.

The d(0.5) value of the particles may be from 26 μm to 40 μm. Particles having a d(0.5) value within this range are typically opaque. Translucent particles are those which allow light to pass through, although it is not possible to see an image through the particles. This is distinguished from transparent compositions which allow light to pass through and an image can be seen through the composition. Methods for determining particle size are well known in the art. For example particle size may be determined using light scattering methodologies, such as using the Mastersizer 2000, Hydro 2000S, Malvern Instruments Limited.

The d(0.5) value of the particles may be from 18 μm to 25 μm. Particles having a d(0.5) value within this range are typically opaque. The d(0.5) value of the particles may be from 10 μm to 15 μm. Particles having a d(0.5) value within this range are typically opaque. In another embodiment, the d(0.5) value of the CSS particles may be from 5 μm to 15 μm.

In another embodiment, the d(0.5) value of the CSS particles may be from 2.5 μm to 4.5 μm. In another embodiment, the d(0.5) value of the CSS particles may be from 5 nm to 20 nm. In another embodiment, the d(0.5) value of the CSS particles may be from 10 nm to 15 nm. In another embodiment, the d(0.5) value of the particles may be from 5 nm to 12 nm.

The d(0.5) or d50 of the particles is the diameter (typically in microns) that splits the distribution with half the population above and half below this diameter. The Dv50 (or Dv0.5) is the median for a volume distribution, Dn50 is used for number distributions, and Ds50 is used for surface distributions. In the present context, d(0.5) will be used to refer to the median particle size for a volume distribution (Dv0.5).

The d(0.1) value of the particles is the diameter that splits the distribution with 10% of the population below and 90% above this diameter.

The d(0.9) value of the particles is the diameter that splits the distribution with 90% of the population below and 10% above this diameter.

A value used to describe the distribution width of the particle size distribution is the span:

Span=($d(0.9)-d(0.1))/d(0.5)$

The span of the core shell silica particles according to the present invention is typically from 1.5 to 3.

In a preferred embodiment, the CSS have a d(0.1) of from 10 to 13 μm, a d(0.5) of from 30 to 33 μm, and a d(0.9) of from 61 to 64 μm.

In another preferred embodiment, the CSS have a d(0.1) of from 6 to 9 μm, a d(0.5) of from 18 to 21 μm, and a d(0.9) of from 41 to 45 μm.

In a further preferred embodiment, the CSS have a d(0.1) of from 3 to 5 μm, a d(0.5) of from 11 to 14 μm, and a d(0.9) of from 33 to 36 μm.

In preferred embodiments, the d(0.5) value of the CSS particles is less than the mean diameter of a human dentin tubule. This allows the CSS particles to enter the dentin tubules, which may be exposed on damage to the protective enamel layer. In human teeth, dentin tubule mean diameter near the dentino-enamel junction is 0.9 the middle section of the dentin tubule has a diameter of about 1.2 μm and near the pulp the diameter is about 2.5 μm.

In another embodiment of the invention, a silica source is selected to produce CSS particles which fits into the dentin tubule (e.g. Aerosil® 200—a fumed silica (synthetic amorphous silica) with a d(0.5) of 0.012 μm). In another embodiment of the invention, the d(0.5) value of the CSS particles is less than 0.9 μm. In still another embodiment of the invention, the CSS particle has a d(0.5) in the range of 0.010 μm-less than 0.9 In another embodiment of the invention, the CSS particles of the invention can also plug, block holes in the enamel.

The present core shell silica particles have surprisingly high surface charge density and ion exchange capacity. In an embodiment, the core shell silica particles have a surface charge density of from 0.5 to 4.5 meq/g silica. In an embodiment, the core shell silica particles have surface charge density of from 2 to 3 meq/g silica. In an embodiment, the core shell silica particles have a surface charge density of 2.45-2.55 meq/g silica.

In an embodiment, the core shell silica particles have a charge, or ion-exchange capacity of, from 0.05 to 0.1 C/cm2 surface area. In an embodiment, the core shell silica particles have a charge, or ion-exchange capacity, of from 0.085 to 0.095 C/cm2 surface area. In an embodiment, the core shell silica particles have a charge, or ion-exchange capacity, of from 0.089 C/cm2 surface area.

In an embodiment of Zn-CSS particles, the amount of zinc adsorbed to surface monolayers of the particles is less than 50% of the maximum ion-exchange capacity of the particle for divalent ions. In an embodiment, the amount of zinc adsorbed to surface monolayers of the particles is 30-35% of the maximum ion-exchange capacity of the particle for divalent ions. In an embodiment, the amount of zinc adsorbed to surface monolayers of the particles is 33% of the maximum ion-exchange capacity of the particle for divalent ions.

In a further aspect, the present invention provides an oral care composition comprising any one of the core shell silica particles described herein.

In one embodiment the composition comprises from 0.01 to 0.5 weight % soluble metal ions. The soluble metal ions may be zinc ions. One of the advantages of the CSS compositions of the present invention is that CSS particles complex with metal ions such that the concentration of free metal ions in solution is low. High concentrations of free metal ions, such as zinc ions can provide disadvantages, particularly for oral care compositions. For example, a high concentration of soluble zinc ions can lead to a poor taste profile for the composition.

In some embodiments, the oral care composition further comprises an orally acceptable carrier.

In an embodiment of the composition, the core shell silica particles comprise a range selected from the ranges consisting of 0.1% to 35 weight %, based on the weight of the composition. In another embodiment of the composition, the CSS particles are present in an amount from 0.1% to 1%. In another embodiment of the composition, the CSS particles are present in an amount from 0.5% wt. % to 20 wt. %, In another embodiment of the composition, the CSS particles are present in an amount from 1% wt. % to 10 wt. %.

In an embodiment, the metal salt is present at 0.01-3.0 weight % of the composition. In an embodiment, the metal salt is present at 0.01-1.5 weight % of the composition. In an embodiment, the metal salt is present at 0.01-1.0 weight %. In an embodiment, the metal salt is present at 0.1-0.5 weight %. In an embodiment, the metal salt is present at 0.1%. In an embodiment, the metal salt is present at 1 weight % or 2 weight %. In an embodiment the metal salt is $ZnCl_2$ in an amount of from 0.5% to 2 weight % of the composition.

In another embodiment of the invention, the composition may take any dosage form useful for oral administration. In an embodiment, the composition is a solid, a paste, a gel, or a liquid.

Illustrative examples of these include, but are not limited to, a dentifrice, e.g., a toothpaste, dental gel, dental cream, or tooth powder; a mouthwash, mouth rinse, or mouth spray; an oral slurry or liquid dentifrice; a gum or other confectionary; a lozenge; dental floss or dental tape; a prophylaxis paste or powder; a mono- or multi-layer oral film or gel strip, e.g., tooth strips or breath strips, preferably using a biodegradable or orally consumable film or gel; functional film or gel flakes or functional micro-, or nano-particles; a film-forming composition comprising pre-gel(s) or pre-polymer(s), e.g., film-forming dentifrices, dental paints; a tooth hardener; or a coating on an oral, e.g., orthodontic, appliance or implant.

For solid dentifrices such as toothpastes, the amount of water in the composition is selected from an amount consisting of less than 10% by weight, less than 5% by weight, less than 1% by weight. In each of these amounts, the lower range for the amount of water is 0% or no more than 0.1% water.

In an embodiment of an oral care composition, the composition further comprises an anti-malodor agent. In an embodiment, the additional anti-malodor compound is a known odor-controlling agent. In addition, other metal-containing compounds, such as those of copper, stannous, bismuth, strontium; and succulents or other ingredients which increase salivary flow, act to wash away odors, are useful in the compositions described herein. Certain strong citrus-based flavorants, odor-absorption complexes, which entrap or adsorb malodor molecules are also useful in the claimed compositions. For example, Ordenone® has the ability to encapsulate malodor molecules such as mercaptans, sulfides and amines within its structure, as disclosed in, for example, U.S. Pat. No. 6,664,254. Odor-controlling actives suitable also include, but are not limited to, enzymes that can interrupt the process by which odors are created. For example, odor-blocking enzymes such as arginine deiminase, can be effectively formulated in the compositions of the invention. Also, molecules that effectively inhibit the bacterial production of malodor molecules can be used to control odor, for example agents that interfere with the bacterial enzymes cysteine desulfhydrase and/or methionine gamma-lyase. Odor-controlling actives suitable for odor blocking or as odor blockers, include but are not limited to agents that act by oxidizing or otherwise chemically reacting with malodor molecules, including peroxides, perchlorites, and reactive molecules with activated double bonds.

The carrier may include, but is not limited to water or other aqueous solvent systems.

The orally acceptable carrier may further comprise a humectant. Possible humectants are ethanol, a polyhydric alcohol, which includes, but is not limited to glycerin, glycol, inositol, maltitol, mannitol, sorbitol, xylitol, propylene glycol, polypropylene glycol (PPG), polyethylene glycol (PEG) and mixtures thereof, or a saccharide, which includes, but is not limited to fructose, glucose, sucrose and mixtures of saccharides (e.g. honey).

The oral care composition may further comprise an anti-bacterial agent, which is not the core shell silica particle described herein. The anti-bacterial agent may be triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate, stannous fluoride, stannous monofluorophosphate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; or mixtures thereof.

In some embodiments, the anti-bacterial agent is present at a concentration selected from the group consisting of from 0.001% to 3%, by weight, 0.05% to 2%, by weight and 0.075% to 1.5% by weight.

Alternatively, there is no additional anti-bacterial agent except for the core shell silica particles of the invention.

In some embodiments, the oral care composition may further include anti-caries agents, desensitizing agents, viscosity modifiers, diluents, surfactants, emulsifiers, foam modulators, pH modifying agents, abrasives, mouth feel agents, sweetening agents, flavor agents, colorants, preservatives, amino acids, anti-oxidants. anti-calculus agents, a source of fluoride ions, thickeners, an active agent for prevention or treatment of a condition or disorder of hard or soft tissue of the oral cavity, adhesive agents, a whitening agent and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Some embodiments of the present invention optionally comprise an amino acid. Suitable amino acids include, but are not limited to arginine, cysteine, leucine, isoleucine, lysine, alanine, asparagine, aspartate, phenylalanine, glutamate, glutamic acid, threonine, glutamine, tryptophan, glycine, valine, praline, serine, tyrosine, and histidine, and a combination of two or more thereof. The amino acids can include R- and L-forms and salt forms thereof. The amino acids (and salt forms thereof) can also include acid ester and/or fatty amide derivatives of the amino acid (e.g. ethyl lauroyl arginate hydrochloride (ELAH)).

An embodiment of the composition optionally comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

An embodiment of the composition optionally comprises an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. The oral composition may include a mixture of different anticalculus agents. In one preferred embodiment, tetrasodium pyrophosphate (TSPP) and sodium tripolyphosphate (STPP) are used. The anticalculus agent comprises TSPP at about 1-2% and STPP at about 7% to about 10%.

An embodiment of the composition optionally comprises at least one orally acceptable source of fluoride ions. Any known or to be developed in the art may be used. Suitable sources of fluoride ions include fluoride, stannous fluoride, sodium fluoride, potassium fluoride, amine fluoride, ammonium fluoride, stannous monofluorophosphate, sodium monofluorophosphate, potassium monofluorophosphate, amine monofluorophosphate, ammonium monofluorophosphate, stannous fluorosilicate, sodium fluorosilicate, potassium fluorosilicate, amine fluorosilicate ammonium fluorosilicate, and mixtures thereof. One or more fluoride ion-releasing compound is optionally present in an amount providing a total of about 100 to about 20,000 ppm, about 200 to about 5,000 ppm, or about 500 to about 2,500 ppm, fluoride ions.

An embodiment of the composition optionally comprises various dentifrice ingredients to adjust the rheology and feel of the composition such as surface active agents, thickening or gelling agents, etc.

An embodiment of the composition optionally comprises a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

An embodiment of the composition optionally comprises a surface active agent (surfactant). Suitable surfactants include without limitation water-soluble salts of C8-C20 alkyl sulfates, sulfonated monoglycerides of C8-C20 fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

An embodiment of the composition optionally comprises a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as Carbowax®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

An embodiment of the composition optionally comprises flavorants, sweeteners, colorants, foam modulators, mouthfeel agents and others additively may be included if desired, in the composition.

An embodiment of the composition optionally comprises one or more further active material(s), which is operable for the prevention or treatment of a condition or disorder of hard or soft tissue of the oral cavity, the prevention or treatment of a physiological disorder or condition, or to provide a cosmetic benefit. Examples of such further active ingredient comprise a sialagogue or saliva-stimulating agent, an anti-plaque agent, an anti-inflammatory agent, and/or a desensitizing agent.

Adhesion enhancing agents can also be added to the oral care compositions which include but are not limited to waxes, inclusive of bees' wax, mineral oil, plastigel, (a blend of mineral oil and polyethylene), petrolatum, white petrolatum, shellac, versagel (blend of liquid paraffin, butene/ethylene/styrene hydrogenated copolymer) polyethylene waxes, microcrystalline waxes, polyisobutene, polyvinyl pyrrolidone/vinyl acetate copolymers, and insoluble polyacrylate copolymers.

Also effective as adhesion enhancing agents are liquid hydrophilic polymers including polyethylene glycols, nonionic polymers of ethylene oxide having the general formula: HOCH2 (CH2OCH2)n1CH2OH wherein n1 represents the average number of oxyethylene groups. Polyethylene glycols available from Dow Chemical are designated by a number such as 200, 300, 400, 600, 2000 which represents the approximate average molecular weight of the polymer, as well as nonionic block copolymer of ethylene oxide and propylene oxide of the formula: HO(C2H4O)a1(C3H6O)b1(C2H4O)c1H. The block copolymer is preferably chosen (with respect to a1, b1 and c1) such that the ethylene oxide constituent comprises from about 65 to about 75% by weight, of the copolymer molecule and the copolymer has an average molecular weight of from about 2,000 to about 15,000 with the copolymer being present in the liquid tooth whitening composition in such concentration that the composition is liquid at room temperatures.

A particularly desirable block copolymer for use in the practice of the present invention is available commercially from BASF and designated Pluraflo L1220 (PEG/PPG 116/66) which has an average molecular weight of about 9,800. The hydrophilic poly(ethylene oxide) block averages about 65% by weight of the polymer.

Synthetic anionic polycarboxylates may also be used in the oral compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the trade name GANTREZ® (methylvinylether/maleic anhydride), e.g., AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the oral composition. Generally, the anionic polycarboxylates is present within the oral composition from about 0.05% to about 4% by weight, preferably from about 0.5% to about 2.5% by weight.

Adhesion enhancing agents employed in compositions of various embodiments of the invention are present in an amount of from about 0 to about 20% by weight. Preferably, the adhesion enhancing agents are present in an amount of from about 2 to about 15% by weight.

An embodiment of the composition optionally comprises a whitening agent which includes, but is not limited to peroxide compounds such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite, pigments or dyes. In some embodiments the whitening agent is separated from the aqueous carrier. In some embodiments the whitening agent is separated from the aqueous carrier by encapsulation of the whitening agent.

In one embodiment of the composition, the composition comprises about 65%-99.9% of the carrier and further included ingredients, i.e. one or more of anti-caries agents, desensitizing agents, viscosity modifiers, diluents, surfactants, emulsifiers, foam modulators, pH modifying agents, abrasives, mouth feel agents, sweetening agents, flavor agents, colorants, preservatives, amino acids, anti-oxidants, anti-calculus agents, a source of fluoride ions, thickeners, an active agent for prevention or treatment of a condition or disorder of hard or soft tissue of the oral cavity, a whitening agent and combinations thereof. In another embodiment of the composition, the composition comprises about 80%-99.5% of the carrier and further included ingredients. In another embodiment of the composition, the composition comprises about 90%-99% of the carrier and further included ingredients.

The description of the optional ingredients above is also intended to include any combination of ingredients.

In some embodiments, thege core shell silica particles described herein may be prepared in accordance with the processes described in US 2016/0338920 or US 2016/0338919, the contents of which are hereby incorporated herein in their entireties.

In an embodiment, the silica used can be any abrasive silica. The silica may be selected from the group consisting of a precipitated silica, a fumed silica and a fused silica.

Precipitated silica includes, but is not limited to Zeodent® 114 and Zeodent® 165 (precipitated silica particles produced by J.M. Huber—chemical name: synthetic amorphous silica), Sylodent® 783 produced by W.R. Grace, Sorbosil® AC-43 produced by Ineos (PQ Corp.)

The silica may be a fumed silica, such as Aerosil 200, produced by Evonik.

In another embodiment, the silica is a fused silica, which includes but is not limited to CAB-O-SIL® HP-60, produced by Cabot Corporation, TECO-SIL® 10 and TECO-SIL® 44css, produced by C-E Minerals, and Spheron P1500 made by the Japanese Glass Co.

Suitable silicas for use in the invention also include colloidal silicas (thickening silicas) having, such as the aerogels Syloid 244 and 266 (available from W. R. Grace Company), Aerosil (available from DeGussa Co.) and pyrogenic silicas sold under the tradename Cab-O-Sils (available from Cabot Corporation). Tixosil 333 and Tixosil 43B (available from Rhodia Ltda.), Zeodent 165 (available from J. M. Huber Corporation).

Other suitable silicas for use in the invention include silica abrasives which in turn include silica gels and precipitated amorphous silicas. These silicas are colloidal particles/particulates having an average particle size ranging from about 3 microns to about 12 microns, and more preferably between about 5 to about 10 microns and a pH range from 4 to 10 preferably 6 to 9 when measured as a 5% by weight slurry.

Illustrative of silica abrasives useful in the practice of the present invention are marketed under the trade designation Sylodent XWA by Davison Chemical Division of W.R. Grace & Co., Baltimore, Md. 21203. Sylodent 650 XWA, a silica hydrogel composed of particulates of colloidal silica having a water content of 29% by weight averaging from about 7 to about 10 microns in diameter.

Other types of silica abrasives suitable for use in the invention include precipitated silicas having a mean particle size of up to about 20 microns, such as Zeodent 115, marketed by J.M. Huber Chemicals Division, Havre de Grace, Md. 21078, or Sylodent 783 marketed by Davison Chemical Division of W.R. Grace & Company.

An average depth of from 1 to 15 nm of silica may be removed from the surface of the silica particle to form the silica core, and metal silicate is formed on top of the silica core. The average depth of silica removed typically increases as the weight ratio for the amount of base to the amount of silica particles increases. The d(0.5) of the silica core may be from 1 to 15 nm less than the d(0.5) of the silica particles of the starting material. The d(0.5) of the silica core may be about 2 nm less than the d(0.5) of the silica particles of the starting material. The d(0.5) particle diameter of the silica core may be about 6 nm less than the d(0.5) of the silica particles of the starting material. There is a greater percentage reduction in particle diameter for rigid silica particles such as fumed silica than for porous silica particles such as high cleaning silica. For example, for fumed silica the percentage reduction in particle diameter (d(0.5)) may be approximately 15%, whilst for porous high cleaning silica the percentage reduction in particle diameter (d(0.5)) may be approximately 0.06%.

The formation of the core shell silica particles of the invention described above can be effected by manipulating the amount of based used, the amount of humectant used, the amount of metal salt used, and varying the temperature of the reaction.

In an embodiment, the end point of the process results when the d(0.5) value of the core shell silica particles formed by the process is at least 5% greater in diameter than the d(0.5) value of the silica (SiO2) starting material. In another embodiment, the core shell silica particle is from 5%-10% greater in diameter than the average particle diameter of the silica starting material.

The core shell silica particles formed may comprise from 0.0 to 0.5 weight % soluble metal ions. The soluble metal ions are preferably soluble zinc ions. As discussed above a low concentration of soluble metal ions, i.e. a low concentration of free metal ions such as zinc ions which can form complex with the CSS can be used to prepare oral care compositions with an improved taste profile.

The formation of the core shell particles can also be monitored by determining the conductivity of the reaction mixture. The end point of the process results when the conductivity of the reaction mixture decreases by at least 250 micro Siemens/cm (µS/cm) because the electric charges transfer from highly mobile ions (NaOH) to much less mobile silica surface (mobility≈0). In yet another embodiment, the end point of the process results when the conductivity of the reaction mixture decreases by 250-400 µS/cm. Typically, the core shell silica particles are formed when the conductivity of the reaction mixture decreases by at least 2 milliSiemens/cm (mS/cm). Usually, the core shell silica particles are formed when the conductivity of the reaction mixture decreases by at least 5 mS/cm.

In some embodiments, the second metal silicate comprises a divalent metal ion comprises at least about 30 wt. %, at least about 40 wt. %, at least about 50 wt. %, at least about 60 wt. %, at least about 70 wt. %, at least about 80 wt. %, or at least about 90 wt. %, of the total metal silicate of the core shell silica particle.

In some embodiments, the d50 of the core shell silica particle is from about 5 nm to about 50 µm.

In further embodiments, the oral care composition has a pH of from about 7.0 to about less than 10.0. In some embodiments, the oral care composition has a pH of from about 7.7 to about 9. In certain embodiments, the oral care composition has a pH of about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2 9.3, 9.4, 9.5, 9.6, 9.7, 9.8, 9.9 or 10.0.

In some embodiments, the oral care composition position further comprises a gel matrix. In some embodiments, the first metal silicate and the core shell silica particle are embedded within the gel matrix. In further embodiments, the gel matrix has a viscosity of from about 50,000 cps to about 1,500,000 cps. In some embodiments, the gel matrix has a viscosity of from about 50,000 cps to about 1,400,000 cps. In some embodiments, the gel matrix has a viscosity of from about 50,000 cps to about 1,300,000 cps. In some embodiments, the gel matrix has a viscosity of from about 50,000 cps to about 1,200,000 cps. In some embodiments, the gel matrix has a viscosity of from about 50,000 cps to about 1,100,000 cps. In some embodiments, the gel matrix has a viscosity of from about 50,000 cps to about 1,000,000 cps. In some embodiments, the gel matrix has a viscosity of from about 50,000 cps to about 900,000 cps. In some embodiments, the gel matrix has a viscosity of from about 50,000 cps to about 800,000 cps. In some embodiments, the gel matrix has a viscosity of from about 50,000 cps to about 700,000 cps. In some embodiments, the gel matrix has a viscosity of from about 50,000 cps to about 600,000 cps. In some embodiments, the gel matrix has a viscosity of from about 50,000 cps to about 500,000 cps. In some embodiments, the gel matrix has a viscosity of from about 50,000 cps to about 400,000 cps. In some embodiments, the gel matrix has a viscosity of from about 50,000 cps to about 100,000 cps. In some embodiments, the gel matrix has a viscosity of from about 50,000 cps to about 90,000 cps. In some embodiments, the gel matrix has a viscosity of from about 50,000 cps to about 80,000 cps. In some embodiments, the gel matrix has a viscosity of from about 50,000 cps to about 70,000 cps. In some embodiments, the gel matrix has a viscosity of from about 55,000 cps to 1,500,000 cps. In some embodiments, the gel matrix has a viscosity of from about 60,000 cps to about 1,500,000 cps.

In some embodiments, the gel matrix has a viscosity of from about 65,000 cps to about 1,500,000 cps. In some embodiments, the gel matrix has a viscosity of from about 70,000 cps to about 1,500,000 cps. In some embodiments, the gel matrix has a viscosity of from about 75,000 cps to about 1,500,000 cps. In some embodiments, the gel matrix has a viscosity of from about 80,000 cps to about 1,500,000 cps. In some embodiments, the gel matrix has a viscosity of from about 85,000 cps to about 1,500,000 cps. In some embodiments, the gel matrix has a viscosity of from about 90,000 cps to about 1,500,000 cps. In some embodiments, the gel matrix has a viscosity of from about 95,000 cps to about 1,500,000 cps. In some embodiments, the gel matrix has a viscosity of from about 100,000 cps to about 1,500,000 cps. In some embodiments, the gel matrix has a viscosity of from about 150,000 cps to about 1,500,000 cps. In some embodiments, the gel matrix has a viscosity of from about 200,000 cps to about 1,500,000 cps. In some embodiments, the gel matrix has a viscosity of from about 250,000 cps to about 1,500,000 cps. In some embodiments, the gel matrix has a viscosity of from about 300,000 cps to about 1,500,000 cps. In some embodiments, the gel matrix has a viscosity of from about 350,000 cps to about 1,500,000 cps. In some embodiments, the gel matrix has a viscosity of from about 400,000 cps to about 1,500,000 cps. In some embodiments, the gel matrix has a viscosity of from about 450,000 cps to about 1,500,000 cps. In some embodiments, the gel matrix has a viscosity of from about 500,000 cps to about 1,500,000 cps. In some embodiments, the gel matrix has a viscosity of from about 550,000 cps to about 1,500,000 cps. In some embodiments, the gel matrix has a viscosity of from about 600,000 cps to about 1,500,000 cps. In some embodiments, the gel matrix has a viscosity of from about 650,000 cps to about 1,500,000 cps. In some embodiments, the gel matrix has a viscosity of from about 700,000 cps to about 1,500,000 cps. In some embodiments, the gel matrix has a viscosity of from about 750,000 cps to about 1,500,000 cps. In some embodiments, the gel matrix has a viscosity of from about 800,000 cps to about 1,500,000 cps. In some embodiments, the gel matrix has a viscosity of from about 850,000 cps to about 1,500,000 cps. In some embodiments, the gel matrix has a viscosity of from about 900,000 cps to about 1,500,000 cps. In some embodiments, the gel matrix has a viscosity of from about 950,000 cps to about 1,500,000 cps. In some embodiments, the gel matrix has a viscosity of from about 1,000,000 cps to about 1,500,000 cps. In some embodiments, the gel matrix has a viscosity of from about 1,050,000 cps to about 1,500,000 cps. In some embodiments, the gel matrix has a viscosity of from about 1,100,000 cps to about 1,500,000 cps. In some embodiments, the gel matrix has a viscosity of from about 1,150,000 cps to about 1,500,000 cps. In some embodiments, the gel matrix has a viscosity of from about 1,200,000 cps to about 1,500,000 cps. In some embodiments, the gel matrix has a viscosity of from about 1,250,000 cps to about 1,500,000 cps. gel matrix has a viscosity of from about 600,000 cps to about 1,500,000

In some embodiments, the gel matrix controls delivery of the first metal silicate and/or the core shell silica particle to a tooth surface. In some embodiments, the gel matrix controls delivery of the first metal silicate and/or the core shell silica particle.

In some embodiments, the first metal silicate is present in an amount of from about 0.1 wt. % to about 5 wt. %, of the oral care composition. In certain embodiments, the first metal silicate is present in an amount of from about 0.1 wt. % to about 4 wt. %. In further embodiments, the first metal silicate is present in an amount of from about 0.15 wt. % to about 3 wt. %. Still further embodiments provide oral care compositions wherein the first metal silicate is present in an amount of from about 0.2 wt. % to about 2 wt. %. Yet other embodiments provide oral care compositions wherein the first metal silicate is present in an amount of from about 0.25 wt. % to about 1.5 wt. %. In some embodiments, the first metal silicate is present in an amount of from about 0.5 wt. % to about 1.25 wt. %. In other embodiments, the first metal silicate is present in an amount of from about 0.55 wt. % to about 1.15 wt. %.

Still further embodiments provide methods of: a) reducing extrinsic stains on a mammalian tooth; b) whitening a mammalian tooth; and c) removing extrinsic stains from a mammalian tooth; the method comprising: administering a composition according to any foregoing claim to an oral surface of a mammal in need thereof.

Other embodiments provide for the use of any one of the compositions described herein for the manufacture of an oral care composition for: a) reducing extrinsic stains on a mammalian tooth; b) whitening a mammalian tooth; and c) removing extrinsic stains from a mammalian tooth. In some embodiments, the mammal is a human.

In a further aspect, the present invention provides a method of reducing or eliminating malodor in the oral cavity of a patient in need thereof, which comprises applying to the oral surfaces of the patient an oral care composition as defined above.

In some embodiments, the mammal includes, but is not limited to, humans and animals (e.g. dogs, cats, horses, cattle, sheep, llamas, etc.).

Embodiments of the present invention are further described in the following examples. The examples are merely illustrative and do not in any way limit the scope of the invention as described and claimed.

EXAMPLES

Example 1

In-vitro whitening efficacy of exemplary compositions of the present invention and comparative compositions are tested via brushing experiments.

Artificially stained bovine enamel samples are brushed with 1:1 silica toothpaste: artificial saliva slurry for 15 minutes. The teeth are rinsed thoroughly and CieLab measurements (L*a*b) are recorded with a handheld spectrophotometer. Bovine enamel with L values between 58 and 64 are used for the study.

Four bovine enamel samples are mounted per tray and two trays are used per test cell. 1:1 test toothpaste: artificial saliva slurry is prepared for each test composition. The bovine enamel samples are brushed for 2 minutes at 120 strokes/min. The teeth are rinsed with DI water and evaluated for L*a*b values with the spectrophotometer. The brushing is repeated 14 times (equivalent to 1 week product use).

The recorded L*a*b values are used to calculate a whitening index (W*). W* incorporates the L, a, and b values to describe how close the measured color is to true white. It is calculated according to the following equation.

$$W^* = (a^2 + b^2 + (L^* - 100)^2)^{1/2}$$

The data described below in Table 1 reports changes in W* value after treatment (ΔW*).

TABLE 1

| Composition | ΔW* |
|---|---|
| None | 1.86 |
| Bound + Freed Silicate | −6.99 |
| Bound Silicate | −6.25 |
| Freed Silicate | −7.12 |

The data described in Table 1 (above) illustrates the improved stain removal and whitening performance provided by the inventive silicates of the present invention.

Example 2

Further studies are conducted to understand the impact of concentration, pH and counter ion association on performance.

As illustrated by the data described in Table 2 (below), silicate concentration has an unexpected impact on stain removal capability.

TABLE 2

| % Na Silicate | ΔW* |
|---|---|
| 0% | 1.86 |
| 0.56% | −7.01 |
| 0.85% | −8.00 |
| 1.13% | −6.76 |
| 5.00% | −4.47 |

Example 3

The effect of pH on whitening performance, as assessed via 10% pH measurements, is illustrated by the data described in Table 3 (below).

TABLE 3

| % Na Silicate | 10% pH | ΔW* |
|---|---|---|
| 0.85% | 7.86 | −8.65 |
| 0.85% | 8.39 | −9.07 |
| 0.85% | 8.70 | −9.80 |
| 0.85% | 10.5 | −4.50 |

Example 4

Described below in Table 4 are several exemplary compositions of the present invention.

TABLE 4

| Ingredient | Ex. 1 | Ex. 2 | Ex. 3 | Ex. 4 | Ex. 5 | Ex. 6 | Ex 7 | Ex 8 |
|---|---|---|---|---|---|---|---|---|
| Thickener(s) | 4.8 | 4.8 | 4.8 | 4.8 | 4.8 | 4.8 | 4.8 | 4.8 |
| Humectant(s) | 46.68 | 47.73 | 26.5 | 46.31 | 45.54 | 44.77 | 45.69 | 45.82 |
| Sweeteners(s) | 0.3 | 0.3 | 0.3 | 0.3 | 0.3 | 0.3 | 0.3 | 0.3 |
| KOH | 1.25 | 0 | 0 | 0 | 0 | 0 | 0 | 0 |
| Acid | 0.5 | 0.5 | 0.5 | 0.5 | 0.5 | 0.5 | 0.35 | 0.22 |

TABLE 4-continued

| Ingredient | Ex. 1 | Ex. 2 | Ex. 3 | Ex. 4 | Ex. 5 | Ex. 6 | Ex 7 | Ex 8 |
|---|---|---|---|---|---|---|---|---|
| Abrasive(s) | 20 | 15 | 15 | 20 | 20 | 20 | 20 | 20 |
| Altered Abrasive | 0 | 5 | 0 | 0 | 0 | 0 | 0 | 0 |
| Surfactant(s) | 2.75 | 2.75 | 2.75 | 2.75 | 2.75 | 2.75 | 2.75 | 2.75 |
| Colorant(s) | 0.5 | 0.5 | 0.5 | 0.58 | 0.58 | 0.58 | 0.58 | 0.58 |
| Flavor(s) | 1.1 | 1.3 | 1.3 | 1.1 | 1.1 | 1.1 | 1.1 | 1.1 |
| Water | 21 | 21 | 0 | 21 | 21 | 21 | 21 | 21 |
| Preservative(s) | 0.8 | 0.8 | 0.8 | 0.8 | 0.8 | 0.8 | 0.8 | 0.8 |
| Fluoride | 0.32 | 0.32 | 0.32 | 0.32 | 0.32 | 0.32 | 0.32 | 0.32 |
| Silicate Rxn Solution | 0 | 0 | 31.23 | 0 | 0 | 0 | 0 | 0 |
| Commercial Silicate | 0 | 0 | 0 | 1.54 | 2.31 | 3.08 | 2.31 | 2.31 |

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising:
a first metal silicate comprising sodium silicate;
an orally acceptable carrier;
a core shell silica particle comprising:
a second metal silicate; and
a silica particle comprising a core having a surface, wherein the surface of the silica core is etched with the second metal silicate, and the second metal silicate comprises a silicate of a monovalent, or multivalent metal ion, wherein the first metal silicate is not bound to the silica, and
wherein the total amount of the first metal silicate and the second metal silicate is from about 0.5 to about 1.5 wt. %, and the oral care composition has a pH of 7.8 to 8.7.

2. The oral care composition according to claim 1, wherein the multivalent metal ion is selected from: $Ca^{2+}$, $Mg^{2+}$, $Zn^{2+}$, $Sn^{2+}$, $Sr^{2+}$, $Al^{3+}$, $Zr^{4+}$, $Ti^{4+}$, $Fe^{3+}$, $Fe^{2+}$, $Mo^{2+}$, $Co^{2+}$, $Ni^{2+}$, $Mn^{2+}$, $Cu^{2+}$, $Pd^{2+}$, $Mo^{2+}$, $Ru^{2+}$; and a combination of two or more thereof.

3. The oral care composition according to claim 2, wherein the multivalent metal ion is selected from $Zn^{2+}$ and $Sn^{2+}$.

4. The oral care composition according to claim 1, wherein the second metal silicate further comprises a monovalent metal ion selected from $Na^+$ and $K^+$.

5. The oral care composition according to claim 1, wherein the silica is selected from: precipitated silica; fumed silica; heat treated precipitated silica; and fused silica.

6. The oral care composition according to claim 1, wherein the oral care composition further comprises a gel matrix.

7. The oral care composition according to claim 6, wherein the first metal silicate and the core shell silica particle are embedded within the gel matrix.

8. The oral care composition according to claim 6, wherein the gel matrix has a viscosity of from about 10,000 cps to about 100,000 cps.

9. The oral care composition according to claim 6, wherein the gel matrix controls the delivery of the first metal silicate and/or the core shell silica particle.

10. The oral care composition according to claim 1, wherein the first metal silicate is present in an amount of from about 0.25 wt. % to about 2 wt. %.

11. The oral care composition according to claim 1, wherein the first metal silicate is present in an amount of from about 0.25 wt. % to about 1.25 wt. %.

12. The oral care composition according claim 1, wherein the first metal silicate is present in an amount of from about 0.5 wt. % to about 1.15 wt. %.

13. The oral care composition according to claim 1, wherein the total amount of the first metal silicate and the second metal silicate is present in an amount of from about 0.5 wt. % to about 1.25 wt. %.

14. The oral care composition according to claim 1, wherein the total amount of the first metal silicate and the second metal silicate is present in an amount of from about 0.55 wt. % to about 1.15 wt. %.

15. A method of:
a) reducing extrinsic stains on a mammalian tooth;
b) whitening a mammalian tooth; and
c) removing extrinsic stains from a mammalian tooth;
the method comprising:
administering a composition according to claim 1 to an oral surface of a mammal in need thereof.

16. An oral care composition comprising:
a first metal silicate comprising sodium silicate;
an orally acceptable carrier; and
a core shell silica particle comprising:
a second metal silicate; and
a silica particle comprising a core having a surface, wherein the surface of the silica core is etched with the second metal silicate, and wherein the second metal silicate comprises a silicate of a monovalent, or multivalent metal ion,
wherein the first metal silicate is not bound to the silica, and wherein the total amount of the first metal silicate and the second metal silicate is from about 0.5 wt. % to about 1.5 wt. %, and the oral care composition has a pH of 7.8 to 8.7, wherein the oral care composition is free of stannous fluorosilicate.

17. The oral care composition according to claim 1, wherein the oral care composition is free of stannous fluorosilicate.

* * * * *